United States Patent [19]

Krufka et al.

[11] Patent Number: 4,765,743
[45] Date of Patent: Aug. 23, 1988

[54] METHOD OF INSPECTING A MASTER MEMBER

[75] Inventors: Frank S. Krufka, Mount Joy; Charles M. Wetzel, Lititz, both of Pa.

[73] Assignee: RCA Licensing Corporation, Princeton, N.J.

[21] Appl. No.: 24,219

[22] Filed: Mar. 10, 1987

[51] Int. Cl.⁴ ............................................. G01B 11/00
[52] U.S. Cl. ..................................... 356/388; 356/389
[58] Field of Search ........................ 356/388, 389, 390

[56] References Cited

U.S. PATENT DOCUMENTS 3,411,007 12/1968 Thompson ........................... 356/388
3,711,205 1/1973 Tulk et al. ........................... 356/389
3,758,326 9/1973 Hennings et al. ..................... 117/37

FOREIGN PATENT DOCUMENTS 0884179 11/1981 U.S.S.R. ............................... 356/389

*Primary Examiner*—R. A. Rosenberger
*Assistant Examiner*—Crystal Cooper
*Attorney, Agent, or Firm*—E. M. Whitacre; D. H. Irlbeck; L. L. Hallacher

[57] ABSTRACT

A method of inspecting a pattern of elements on a working plate includes producing a negative copy of the working plate and aligning the negative copy with a positive inspection plate having elements slightly larger than the elements of the working plate whereby flaws are revealed as light transmissive spots. The working plate and a negative inspection plate, having the elements slightly smaller than the elements of the working plate, are aligned and flaws are revealed as light transmissive spots.

5 Claims, 2 Drawing Sheets

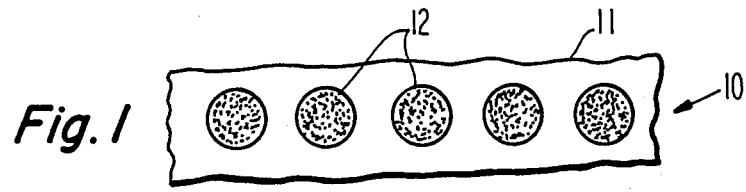
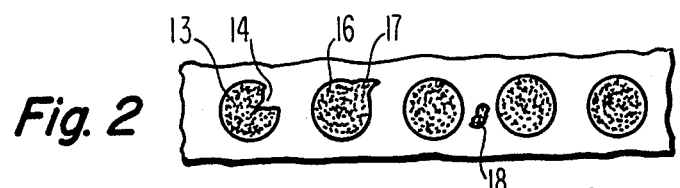
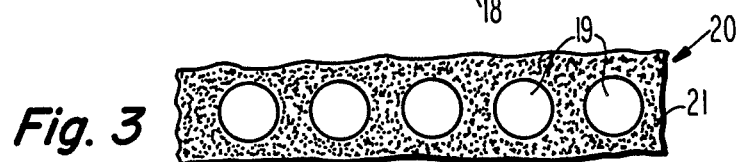
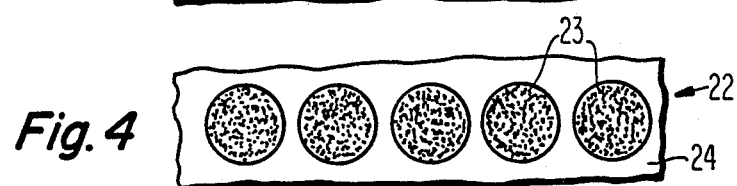
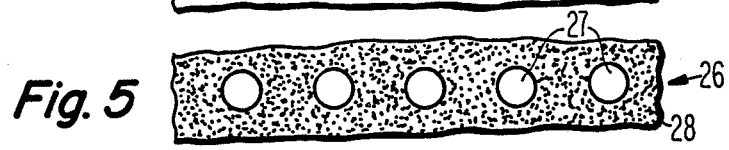
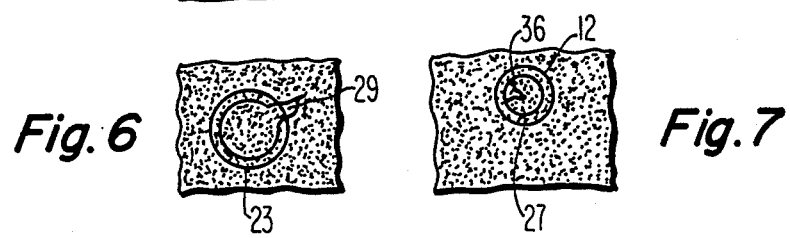

METHOD OF INSPECTING A MASTER MEMBER

BACKGROUND

This invention relates generally to inspection methods and particularly to a method of inspecting a pattern of elements on a working member.

Many products of industry are made by chemical etching processes. Examples of such products are integrated circuits and shadow masks for color television tubes. Typically, in the production of such parts, the material of which the part is to be made is covered with a coating of photosensitive material. A pattern of the part is photographically produced on the photosensitive material by exposing the material to light through the pattern, which is present on a rigid, transparent plate. The unexposed photosensitive material is washed away leaving the pattern on the bare part material. The pattern is chemically etched to remove or to lineate, the portion of the part material which has been made bare by washing away the unexposed photosensitive material. Typically, the pattern is photographically produced on the material by the use of a working member, or plate, upon which a very accurate pattern was previously produced. The working plate thus is used to produce a large number of parts. However, during use the working plate degradates and is worn and sometimes is damaged creating a need for replacement plates. For this reason, the working plates are produced from a precisely accurate master plate which is not used to produce parts. Prior to using the working plates to produce parts they are inspected to ensure that they are suitable for producing acceptable parts.

Presently, the working plates are inspected by using a scanner which projects a magnified image onto a viewing screen. Typically, the entire pattern can not be projected onto the screen and therefore the pattern moves across the viewing screen while an operator views the image. This method is subject to operator error because of the movement of the pattern across the screen. Also, for complicated patterns the inspection can require two to four hours leading to substantial operator fatigue. Operator error and fatigue frequently result in defects passing detection by the operator. For this reason, there is a need for a method of inspecting working plate patterns which is rapid and efficient in detecting all defects and which does not subject the operator to substantial fatigue. The invention fulfills these long felt needs.

SUMMARY

A method of inspecting a pattern of elements on a working member includes the steps of aligning a negative copy of the working member and a positive inspection plate having elements slightly larger than the elements in the working member whereby flaws show as light transmissive spots. The working member and a negative inspection plate, having elements slightly smaller than the elements in the working member are aligned, whereby flaws show as light transmission spots.

BRIEF DESCRIPTION OF THE DRAWINGS

FIG. 1 shows a small portion of a working plate to be inspected.

FIG. 2 shows the type of flaws which can occur in the elements of the working plate of FIG. 1.

FIG. 3 is a small portion of a negative film copy of the working plate of FIG. 1.

FIG. 4 is a small portion of a positive inspection plate having enlarged elements.

FIG. 5 is a small portion of a negative inspection plate having smaller elements.

FIG. 6 shows how one type of flaw is detected utilizing the claimed invention.

FIG. 7 shows how another type of flaw is detected using the claimed invention.

DETAILED DESCRIPTION

Figure 8:
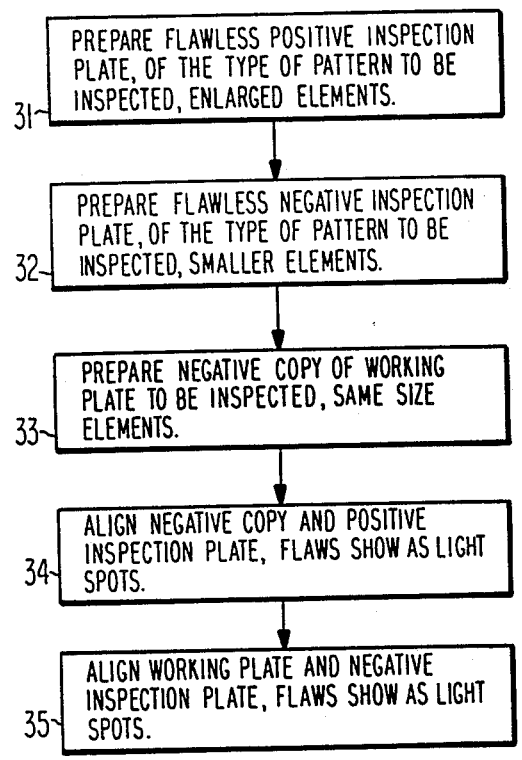
FIG. 8 is a flow chart of a preferred embodiment.

FIG. 1 shows a portion of a working member 10 used to produce photographic images on a piece of material from which a part is to be fabricated by chemical etching. The working plate 10 includes a rigid, transparent substrate 11 upon which a plurality of opaque elements 12 has been printed by any of several well known means. The working plate 10 is used to photographically produce images on the material from which a part is to be fabricated by passing light through the transparent substrate 11 while the opaque elements 12 block light. When the article to be produced is a shadow mask for a color television tube, the opaque elements 12 represent the holes which will be etched into the shadow mask. In such an instance, a large number of the opaque elements 12 are arranged in rows and columns with the elements in adjacent rows being centered between the spaces between successive elements in the previous row.

Because the working plate is used to manufacture a large number of articles, it is essential that all the opaque elements are acceptable, and that the substrate 11 is free of extraneous matter. Accordingly, the working plate 10 must be inspected prior to being used to produce parts. FIG. 2 shows some types of flaws which can occur and cause the production of unacceptable shadow masks, or other parts. An opaque element 13 is not completely formed and has a small missing area 14. Similarly, an opaque element 16 includes an extra portion 17. Another type of flaw which can occur is a splash, or debris mark, 18 which is on the transparent plate between two of the opaque elements.

In preparation of inspecting for the types of defects 14, 17 and 18 of FIG. 2, several components are first produced. FIG. 3 shows a portion of a negative photograph of the working plate to be inspected. This negative is produced on regular photographic film. The film photograph is a negative and, accordingly, the elements 19 are transparent and the material 21 surrounding the elements 19 is opaque. However, the photograph is a one-for-one reproduction and accordingly the transparent elements 19 of the film 20 are the same size as the opaque elements 12 of the working plate 10. A negative film reproduction 20 therefore is made for every individual working plate to be inspected.

FIG. 4 shows a portion of a positive inspection plate 22, which also is prepared prior to inspecting any working plates. The positive inspection plate 22 includes opaque elements 23 which are larger than the opaque elements 12 in the working plate 10 to be inspected. However, the center-to-center spacing of the opaque elements 23 is equal to the center-to-center spacing of the opaque elements 12 of the working plate 10. The material 24 surrounding the opaque elements 23 is transparent to light and preferably is of a rigid material, such as glass. The positive inspection plate 22 is optimized and is made for a particular type of working plate 10 so that the positive inspection plate 22 is useful in inspecting any number of working plates 10 of a particular type.

FIG. 5 shows a portion of a negative inspection plate 26 which is also useful in inspecting any number of working plates 10 of a particular type. The negative inspection plate 26 includes a plurality of transparent elements 27 surrounded by opaque material 28. The transparent elements 27 have a diameter which is slightly smaller than the diameters of the opaque elements 12 in the working member 10. The center-to-center spacing of the transparent elements 27 of the negative inspection plate 26 is identical to the center-to-center spacing of the opaque elements 12 of the working plate 10.

The difference between the diameters of the opaque elements 23 in the transparent inspection plate 22 and the opaque elements 12 in the working plate 10 is dependent upon the allowable tolerance in the dimensions of the opaque elements 12. The difference between the diameter of the transparent elements 27 in the negative inspection plate 26 and the diameter of the opaque elements 12 also is dependent upon the allowable tolerance of the opaque elements 12. When the working plate 10 is used to produce the apertures for high definition television tubes the elements 12 typically will have a diameter of 4.5 mils (0.01 cm). The difference between the diameter of the elements 12 and those of the elements 23 and 27 will then be in the order of 0.2 to 0.4 mil (0.0005 to 0.001 cm).

The inventive method is shown in flow chart form in FIG. 8. At step 31, a flawless positive inspection plate 22 described with respect to FIG. 4, is prepared by any one of several known methods is prepared. At step 32 the flawless negative inspection plate 26 described with respect to FIG. 5 is prepared. At step 33, the negative copy 20 of the working plate 10 of FIG. 1 is prepared. This negative copy is useful only for inspecting the particular working plate from which the negative is produced.

At step 34, the negative copy 20 of FIG. 3 is aligned with the positive inspection plate 22 shown in FIG. 4. The alignment of the negative 20 and positive plate 22 can be done manually using reference marks placed around the edges of the elements 20 and 22. Alternatively, mechanical alignment members, such as alignment bars and pins, can be used or, automatic aligning equipment can be used, all within the purview of one skilled in the art. The negative film copy 20 is opaque with transparent elements 19. The positive inspection plate 22 is transparent with opaque elements 23, and the opaque elements 23 are slightly larger than the transparent elements 19 in the film 20. Accordingly, when all the elements 19 and 23 are aligned, the entire surface layered composite is opaque and will transmit no light. However, if either the substrate 11 or any of the elements 12 of the working plate 10 contains a flaw, such as one the flaws 17 or 18 shown in FIG. 2, the corresponding transparent element 19, or the film material 21 of the negative copy 20 will include a similar flaw because the negative 20 is a direct reproduction of the working plate 10. Accordingly, as demonstrated in FIG. 6, a small portion 29 of the flaw will be transmissive of light and will be immediately visible to an inspector. FIG. 6 also shows how the difference in diameters of the opaque elements 23 and the light transmitting elements 19 must be within acceptable tolerances because a very slight enlargement of an element 12 can fall within the variable diameter of the element 23. When the working plate 10 includes a flaw similar to the flaw 18 of FIG. 2, the negative film copy 20 will have a light transmissive area corresponding to the flaw 18. Accordingly, upon alignment of the negative copy 20 and the transparent inspection plate 22, light will shine through the transmissive area caused by the flaw 18 and will be immediately visible to an inspector.

In FIG. 8, at step 35 the actual working plate 10 is aligned with the negative inspection plate 26. Again, because the working plate 10 is transparent with opaque elements 12, while the negative inspection plate 26 is opaque with transparent elements 27 the alignment of the two components results in a totally opaque structure, in the absence of any flaws. If any of the elements 12 in the working plate 10 includes a flaw of the type 14 in FIG. 2 a transparent portion 36 in FIG. 7 will allow light to pass through the layered elements. The flaw 14 thus will be easily visible to an inspector and indicates that the working plate 10 should be rejected or repaired.

Upon the detection of any flaws of the type 14, 17 or 18 of FIG. 2 the working plate 10 can be repaired, or if the flaw is excessive the entire working plate must be scrapped.

What is claimed is:

1. A method of inspecting a pattern of elements on a working member comprising the steps of:
    aligning a negative copy of said working member and a positive inspection plate having elements slightly larger than the elements on said working member whereby flaws, in the form of extra element portions and splashes between said elements, show as light transmissive spots; and
    aligning said working member and a negative inspection plate having elements slightly smaller than the elements on said working member whereby flaws, in the form of missing element portions, show as light transmissive spots.

2. The method of claim 1 wherein said working member is transparent and elements are opaque.

3. The method of claim 1 wherein said working member is opaque and said elements are transparent.

4. The method of claim 1 wherein said working member is a rigid plate for producing the art work used to produce shadow masks for color television tubes.

5. The method of claim 1 wherein the differences between the dimensions of said element on said working member and the elements on said positive and negative inspection plates are substantially equal to the permissible tolerances of an object to be formed using said working member.

* * * * *